US007776582B2

(12) United States Patent
Armstrong et al.

(10) Patent No.: US 7,776,582 B2
(45) Date of Patent: Aug. 17, 2010

(54) OPTICALLY ENHANCED CHIRAL IONIC LIQUIDS

(75) Inventors: Daniel W. Armstrong, Arlington, TX (US); Jie Ding, Waunakee, WI (US)

(73) Assignee: Sigma-Aldrich Co., St. Louis, MO (US)

( * ) Notice: Subject to any disclaimer, the term of this patent is extended or adjusted under 35 U.S.C. 154(b) by 0 days.

(21) Appl. No.: 12/331,108

(22) Filed: Dec. 9, 2008

(65) Prior Publication Data

US 2009/0145197 A1    Jun. 11, 2009

Related U.S. Application Data

(63) Continuation of application No. 11/177,093, filed on Jul. 8, 2005, now abandoned.

(60) Provisional application No. 60/586,782, filed on Jul. 9, 2004.

(51) Int. Cl.
*C12P 41/00* (2006.01)
(52) U.S. Cl. ..................................................... 435/280
(58) Field of Classification Search ................... 435/280
See application file for complete search history.

(56) References Cited

U.S. PATENT DOCUMENTS

| 2,865,964 | A | 12/1958 | Dornfeld et al. | .......... | 260/606.5 |
|---|---|---|---|---|---|
| 4,948,395 | A | 8/1990 | Armstrong | ...................... | 95/88 |
| 5,064,944 | A | 11/1991 | Armstrong | ................ | 536/123.1 |
| 6,531,241 | B1 | 3/2003 | McEwen | ...................... | 429/46 |
| 6,900,313 | B2 * | 5/2005 | Wasserscheid et al. | ......... | 544/59 |
| 2001/0031875 | A1 | 10/2001 | Kitazume | .................... | 546/347 |
| 2006/0014955 | A1 | 1/2006 | Armstrong et al. | ............. | 546/79 |
| 2006/0025598 | A1 | 2/2006 | Armstrong et al. | ........... | 548/101 |
| 2008/0027231 | A1 | 1/2008 | Armstrong et al. | ........ | 548/313.7 |
| 2008/0210858 | A1 | 9/2008 | Armstrong et al. | ........... | 250/282 |

FOREIGN PATENT DOCUMENTS

| CN | 1383920 | 5/2004 |
|---|---|---|
| CN | 1383921 | 6/2004 |
| DE | 39618 | 6/1965 |
| EP | 0 137 241 | 4/1985 |
| GB | 711654 | 7/1954 |
| GB | 821242 | 10/1959 |
| JP | 2003/017148 | 1/2003 |
| JP | 2004269414 A | 9/2004 |
| JP | 2004277351 | 10/2004 |
| WO | WO 91/04668 | 4/1991 |
| WO | WO 01/85093 | 11/2001 |
| WO | WO 2005/054241 | 6/2005 |
| WO | WO 2006/012513 | 2/2006 |
| WO | WO 2007/124397 | 11/2007 |
| WO | WO 2008/110007 | 9/2008 |
| WO | WO 2009/103062 | 8/2009 |
| WO | WO 2009/103064 | 8/2009 |

OTHER PUBLICATIONS

Armstrong et al. Anal. Chem, 1999, 71, 3873-3876.*
Adams CJ, et al., "Friedel-Crafts reactions in room temperature ionic liquids", *Chem. Comm.*, 2097-2098 (1998).
Allen CR, et al., Facile synthesis of ionic liquids possessing chiral carboxylates, Tetrahedron Lett. 47:7367-7370 (2006).
Anderson JL, et al., "High-stability ionic liquids. A new class of stationary phases for gas chromatography", *Anal. Chem.*, 75(18):4851-4858 (2003).
Arimura T, et al., *Template Effects On Calixarene Conformations Through Host-Guest Type Interactions*, Tetrahedron Lett. 30(19):2563-2566 (1989).
Armstrong DW, et al., "Examination of ionic liquids and their interaction with molecules, when used as statioanry phases in gas chromatography", *Anal. Chem.*, 71(17):3873-3876 (1999).
Bao W, et al., "Synthesis of chiral ionic liquids from natural amino acids", *J. Org. Chem.*, 68:591-593 (2003).
Barber DW, et al., "The chromatography of gases and vapours. Part VI. Use of the stearates of bivalent manganese, cobalt, nickel, copper, and zinc as column liquids in gas chromatography", *Am. J. Chem. Soc.*, 18-24 (1959).
Baudequin C, et al., "Ionic liquids and chirality: oppportunities and challenges", *Tet. Asym.*, 14:3081-3093 (2003).
Berthod A, et al., "Ionic liquids as stationary phase solvents for methylated cyclodetrins in Gas Chromatography", *Chromatographia*, 53:63 (2001).
Biedron et al., "Ionic liquids as reaction media for polymerization processes; atomic transfer radical polymerization (ATRP) of acdrylates in ionic liquids", *Polym. Int.*, 52:1584-1588 (2003).
Bitterer F, et al., "Tertiary Alkylphosphanes with Ammonium Groups in the Side Chains—Amphiphiles with Basic P Atoms", *Inorganic Chemistry*, 275-279, (1995).
Branco LC, et al., "Highly selective transport of organic compounds by using supported liquid membranes based on ionic liquids", *Angew. Chem. Int. Ed. Engl.*, 41(15):2771-2773 (2002).
Brophy JJ et al., "The Cleavage of Bisphosphonium Salts by Sodium Hydride", *Chemical Communications*, 531-532, (1966).
Carmichael AJ, et al., "Ionic Liquids: Improved syntheses and new products", *ACS Symposium Series*, 856:14-31 (2003).
Chauvin Y, et al., "A novel class of versatile solvents for two-phase catalysis: hydrogenation, isomerization, and hydroformylation of alkenes catalyzed by rhodium complexes in liquid 1,3-dialkylimidazolium salts", *Angew. Chem. Int. Ed. Engl.*, 34:2698-2700 (1995).
Chellappan K, et al., *A Calix[4]Imidazolium[2]Pyridine as an Anion Receptor*, Angew. Chem. Int. Ed. 44(19):2899-2903 (2005).
Cornils B, et al., *Aqueous-Phase Organometallic Catalysis: Concepts and Applications*, Wiley-VCH: Weinheim, 555-563, (1998).
"Cyclodextrin stationary phases for chiral separations and highly selective achiral separations", *Chiraldex Handbook*, 6th Ed., Advanced Separation Technologies, 8 (2002).

(Continued)

*Primary Examiner*—D. Margaret Seaman
*Assistant Examiner*—Nizal S Chandrakumar
(74) *Attorney, Agent, or Firm*—Harness, Dickey & Pierce, P.L.C.

(57) ABSTRACT

The invention relates to the use of optically enhanced chiral ionic liquids, particularly for gas chromatography and as a reaction solvent. Specific optically enhanced chiral cationic liquids are described as is a class of optically enhanced chiral anionic liquids.

10 Claims, No Drawings

OTHER PUBLICATIONS

Earle MJ, et al., "Diels-Alder reactions in ionic liquids: A safe recyclable alternative to lithium perchlorate-diethyl ether mixtures", *Green Chem.*, 23-25 (1999).

Fischer T, et al., "Diels-Alder reactions in room-temperature ionic liquids", *Tet. Lett.*, 40:793-796 (1999).

Furton KG, et al., "Solute-solvent interactions in liquid alkylammonium 4-toluenesulfonate salts studied by gas chromatography", *Anal. Chem.*, 59(8):1170-1176 (1987).

Handy ST, "Greener solvents: room temperature ionic liquids from biorenewable sources", *Chemistry—A European Journal*, 9(13):2938-2944 (2003).

Haramoto Y, et al., "Liquid crystal properties of new ionic liquid crystal compounds having a 1,3-dixane ring", *Liquid Crystals*, 29(1):87-90 (2002).

Harris, Quantitative Chemical Analysis, Ch. 23, p. 641-674 (1999).

Herrmann WA, et al., "Chiral heterocyclic carbenes in asymmetric homogenous catalysis", *Angew. Chem. Int. Ed. Engl.*, 35:2805-2807 (1996).

Hideg K and Hankovszky OH, *Benzazoles, III. Alkylation of Benzimidazoles*, Acta Chimica Academiae Scientarum Hungaricae 49(3):303-310 (1966).

Hong-Yang et al, *Design and synthesis of novel chiral liquids and their application in free radical polymerization of methyl methacrylate* Chinese Journal of Polymer Science 21(3) 265-270, (2003).

Horn PE, et al., "The Reactions of Organic Derivatives of Elements Capable of Valency-Shell Expansion. Part VII. Further Experiments with Quaternary Phosphonium Salts", *Journal of the Chemical Society*, 1036-1044, (1963).

Howell BA, et al., *High phosphorus/bromine content compounds as polyolefin flame retardants*, Recent Advances in Flame Retardancy of Polymeric Materials, 7:119-126 (1997).

Howarth J, et al., "Moisture stable dialkylimidazolium salts as heterogeneous and homogeneous lewis acids in the Diels-Alder reaction", *Tet. Lett.*, 38(17):3097-3100 (1997).

Hu X, et al., *A Bis-Carbenealkenyl Copper(I) Complex from a Tripodal Tris-Carbene Ligand*, Organometallics 22(15):3016-3018 (2003).

Hu X, et al., *Copper Complexes of Nitrogen-Anchored Tripodal N-Heterocyclic Carbene Ligands*, J. Am. Chem. Soc. 125(40):12237-12245 (2003).

Hu X, et al., *Dioxygen Activation by a Low-Valent Coblat Complex Employing a Flexible Tripodal N-Heterocyclic Carbene Ligand*, J. Am. Chem. Soc. 126(41):13464-13473 (2004).

Hu X, et al., *Group II Metal Complexes of N-Heterocyclic Carbene Ligands: Nature of the Metal-Carbene Bond*, Organometallics 23(4):755-764 (2004).

Hu X, et al., *Silver Complexes of a Novel Tripodal N-Heterocyclic Carbene Ligand: Evidence for Significant Metal-Carbene π-Interaction*, Organometallics 22(4):612-614 (2003).

Hu X, et al., *Terminal Cobalt(III) Imido Complexes Supported by Tris(Carbene) Ligands: Imido Insertion into the Cobalt-Carbene Bond*, J. Am. Chem. Soc. 126(50):16322-16323 (2004).

Huddleston JG, et al., "Room temperature ionic liquids as novel media for "clean" liquid-liquid extraction", *Chem. Comm.*, 1765-1766 (1998).

Ilies MA, et al., *Lipophilic Pyrylium Salts in the Synthesis of Efficient Pyridinium-Based Cationic Lipids, Gemini Surfactants, and Lipophilic Oligomers for Gene Delivery*, J. Med. Chem. 49(13):3872-3887 (2006).

Ishida Y, et al., "Design and synthesis of a novel imidazolium-based ionic liquid with planar chirality", *Chem. Comm.*, 2240-2241 (2002).

Jodry JJ, et al., "New chiral imidazolium ionic liquids: 3D-network of hydrogen bonding", *Tet. Lett.*, 45:4429-4431 (2004).

Kawahara S and Uchimaru T, *One-Pot Preparation of o-Xylylene Diamine and its Related Amines*, Zeitschrift Fuer Naturforschung, B: Chemical Sciences, 55(10):985-987 (2000).

Kim H and Kang J, *Iodide Selective Fluorescent Anion Receptor with Two Methylene Bridged Bis-Imidazolium Rings on Naphthalene*, Tetrahedron Lett. 46(33):5443-5445 (2005).

Kiss L, et al., "Further insight into the mechanism of Heck oxyarylation in the presence of chiral ligands", *ARKIVOC*, v:69-76 (2003).

Kostyanovskii RG, et al., Geminal systems. 19. Reactions of Aminomethylphosphines with Electrophilic Reagents, *Bulletin of the Academy of Sciences of the USSR, Division of Chemical Sciences*, 1433-1441, (1983).

Kwon JY, et al., *Fluorescent GTP-Sensing in Aqueous Solution of Physiological pH*, J. Am. Chem. Soc. 126(29):8892-8893 (2004).

Lane ES, et al., *Quaternary ammonium nitrates. Part II. Reaction of nitratoalkyl ethers, amines, amides, and urethanes with tertiary amines and related compounds* J. Chem. Soc. 2006-2010 (1956).

Lee CW, "Diels-Alder reactions in chloroaluminate ionic liquids acceleration and selectivity enhancement", *Tet. Lett.*, 40:2461-2462 (1999).

Levillain J, et al., "Synthesis and properties of thiazoline based ionic liquids derived from the chiral pool", *Chem. Comm.*, 2914-2915 (2003).

Liu J, et al., *Imidazolylidene Carbene Ligated Palladium Catalysis of the Heck Reaction in the Presence of Air*, Org. Biomol. Chem. 1(18):3227-3231 (2003).

Löhr HG, et al., *Organylammonium-Wirtsubstanzen als vielseitige Clathratbildner*, Chem. Ber. 117(4):1487-1496 (1984).

Ludley P, et al., "Phosphonium tosylates as solvents for the Diels-Alder reaction", *Tet. Lett.*, 42:2011-2014 (2001).

Lundberg KL et al., "Gem-Dibasic Ligands with Phosphorus, Sulphur and Nitrogen Sites, and Some Borane Derivatives", *Inorganic Chemistry*, 1336-1340, (1969).

Mamane V, et al., *Palladium-Catalyzed Cross-Coupling Reaction of a Chiral Ferrocenyl Zinc Reagent with Aromatic Bromides: Application to the Design of Chiral Octupoles for Second Harmonic Generation*, Synthesis 3:455-467 (2003).

Mas-Marzá E, et al., *Carbene Complexes of Rhodium and Iridium from Tripodal N-Heterocyclic Carbene Ligands: Synthesis and Catalytic Properties*, Inorg. Chem. 43(6):2213-2219 (2004).

Mas-Marzá E, et al., *Synthesis and Catalytic Properties of Two Trinuclear Complexes of Rhodium and Iridium with the N-Heterocyclic Tris-carbene Ligand TIMEN$^{iPr}$*, Organometallics 24(13):3158-3162 (2005).

McCullough D, et al., *Glued Langmuir-Blodgett Bilayers from Porous Versus Nonporous Surfactants*, J. Am. Chem. Soc. 126(32):9916-9917 (2004).

Mizzoni RH, et al., *Polyamine Salts with Autonomic Blocking Properties*, J. Am. Chem. Soc. 76:2414-2417 (1954).

Molodykh ZV, et al., *Antimicrobial Activity of Ortho-Aminomethylphenols and Their Derivatives*, Pharm. Chem. J. 21(2):110-114 (1987).

Ohki A, et al., *Sensing of Poly(Styrenesulfonate)s by Polymeric Membrane Electrodes Based on Liquid Anion-Exchangers*, Bull. Chem. Soc. Jpn., 70(4):799-804 (1997).

Pacholec F, et al., "Molten organic salt phase for gas-liquid chromatography", *Anal. Chem.*, 54(12):1938-1941 (1982).

Parenty ADC, et al., *General One-Pot, Three-Step Methodology Leading to an Extended Class of N-Heterocyclic Cations: Spontaneous Nucleophilic Addition, Cyclization, and Hydride Loss*, J. Org. Chem. 69(18):5934-5946 (2004).

Patinec V, et al., *The Use of Triquaternary Alkylammonium Ions in the Synthesis of STA-5, a Magnesioaluminophosphate with the BPH Framework* Topology, Chemistry of Materials 11(9):2456-2562 (1999).

Patrascu C, et al., "New pyridinium chiral ionic liquids", *Heterocycles*, 63:2033-2041 (2004).

Payagala T, et al., "Unsymmertrical Dicationic Ionic Liquids: Manipulation of Physiochemical Properties Using Specific Structural Architectures", *Chemistry of Materials*, 5848-5850, (2007).

Pégot B, et al., "First application of chiral ionic liquids in asymmetric Baylis-Hillman reaction", *Tet. Lett.*, 45:6425-6428 (2004).

Pomaville RM, et al., "Solute-solvent interactions in liquid tetrabutylammonium sulfonate salts studied by gas chromatography", *Anal. Chem.*, 60(11):1103-1108 (1988).

Poole CF, et al., "Chemometric evaluation of the solvent properties of liquid organic salts", Analyst, 120:289-294 (1995).

Poole CF, et al., "Survey of organic molten salt phases for gas chromatography", *J. Chromatography*, 289:299-320 (1984).

Rehse K and Kämpfe M, *Oligotertiäre Amines and Oligotertiäre Ammoniumsalze*, Archiv Der Pharmazie 322:811-815 (1989).

Remsburg et al., "Evaluation of Dicationic Reagents for Their Use in Detection of Gas Phase Ion Association", *Journal of the American Society for Mass Spectrometry*, 261-269, (2007).

Schilf W, et al., *NMR and X-ray Investigations of Model Tris- and Bis-Pyridinium Fluoroborates*, J. Mol. Struct. 707(1-3):115-121 (2004).

Shinkai S, et al., *Ion Template Effects on the Conformation of Water-Soluble Calixarenes*, J. Org. Chem. 56(1):295-300 (1991).

Soai K, et al., "Chiral quaternary ammonium salts as solid-state catalysts for the enantioselective addition of diethylzinc to aldehydes", *Chem. Comm.*, 1:43-44 (1990).

Soukup-Hein RJ, et al., *Evaluating the Use of Tricationic Reagents for the Detection of Doubly Charged Anions in the Positive Mode by ESI-MS*, Anal. Chem.80(7):2612-2616 (2008).

Stark A, et al., "1-Ethyl-3-methylimidazolim halogenoaluminate ionic liquids as solvents for Friedel-Crafts acylation reactions of ferrocene", *J. Chem. Soc., Dalton Trans.*, 63-66 (1999).

Suarez PAZ, et al., "The use of new ionic liquids in two-phase catalytic hydrogenation reaction by rhodium complexes", *Polyhedron*, 15(7):1217-1219 (1996).

Thanh G, et al., Solvent-free microwave-assistant preparation of chiral ionic liquids from (-)-Nmethylephedrine, *Eur. J. Org. Chem.*, 5:1112-1116 (2004).

Tosoni M, et al., "Synthesis of novel chiral ionic liquids and their phase behavior in mixtures with smectic and nematic liquid crystals", *Helv. Chim. Acta*, 87:2742-2749 (2004).

Ujiie S, et al., "Ion complex type of novel chiral smectic C liquid crystal having chiral hydrogen tartrate counterion", *Chem. Lett.*, 23(1):17-20 (1994).

Wang Y, *Synthesis and application of novel chiral ionic liquids derived from α-Pinene*, Masters Thesis, New Jersey Institute of Technology, Department of Chemistry and Environmental Science, (2003).

Wasserscheid P, et al., "Synthesis and properties of ionic liquids derived from the chiral pool", *Chem. Comm.*, 200-201 (2002).

Wong WWH, et al., *Tetrakis(imidazolium)Macrocyclic Receptors for Anion Binding*, Org. Biomol, Chem. 3(23):4201-4208 (2005).

Zhao et al., *Suzuki Cross-Coupling Mediated by Tetradentate N-Heterocyclic Carbene (NHC)-Palladium Complexes in an Environmentally Benign Solvent*, Org. Biomol. Chem. 1(10):1643-1646 (2003).

Office Action, dated Sep. 9, 2008 issued in U.S. Appl. No. 11/177,093.

Office Action, dated Sep. 17, 2008 issued in U.S. Appl. No. 11/701,537.

Office Action, dated Sep. 22, 2008 issued in U.S. Appl. No. 11/187,389.

Office Action, dated May 6, 2009 issued in U.S. Appl. No. 11/701,537.

Office Action, dated May 8, 2009 issued in U.S. Appl. No. 11/187,389.

Office Action, dated Sep. 9, 2009 issued in U.S. Appl. No. 11/701,537.

International Search Report, PCT/US2005/26036, dated Jun. 16, 2006.

International Search Report, PCT/US2005/24188, dated Feb. 5, 2007.

International Search Report, PCT/US2008/052590, dated Mar. 4, 2009.

International Search Report, PCT/US2008/052583, dated Mar. 25, 2009.

International Search Report, PCT/US2009/034293, dated Apr. 15, 2009.

International Search Report, PCT/US2009/034290, dated Apr. 21, 2009.

International Search Report, PCT/US2008/052583, dated Sep. 18, 2009.

\* cited by examiner

OPTICALLY ENHANCED CHIRAL IONIC LIQUIDS

CROSS REFERENCE TO RELATED APPLICATIONS

This application is continuation of U.S. application Ser. No. 11/177,093 filed 8 Jul. 2005, which claims priority to U.S. Provisional Application No. 60/586,782 filed 9 Jul. 2004. The disclosures of the above applications are incorporated herein by reference.

BACKGROUND OF THE INVENTION

Nonchiral ionic liquids have been used as solvents in the past. Chiral liquids that are racemic have been used as solvents as well. See Yasuhiro Ishida et al., "*Design and synthesis of a novel imidazolium-based ionic liquid with planar chirality*," Chem. Commun. 2240-41 (2002) (a copyright of the Royal Society of Chemistry). Solvents of enantiomerically enhanced chiral cations have also been described. See Wasserscheid et al., "*Synthesis and properties of ionic liquids derived from the 'chiral pool'*," Chem. Commun. 200-01 (2002) and Weiliang Bao et al., "*Synthesis of Chiral Ionic Liquids from Natural Amino Acids,*" 68 J. Org. Chem. 591 (2003). These were not described as vehicles for conducting subsequent reactions.

Earle et al. disclosed reactions of dienes and dienophiles in various solvents including [bmim] [lactate], an ionic liquid with a chiral anion of unreported configuration or purity. The result was not asymmetric. See Martyn J. Earle et al., "*Diels-Alder reactions in ionic liquids*," Green Chem. 23-25 (1999). Chiral nonionic materials have also been used as the stationary phases in gas chromatography. (See U.S. Pat. Nos. 4,948,395 and 5,064,944.)

SUMMARY OF THE INVENTION

The present invention relates to optically enhanced chiral ionic liquids ("OCIL"). These are salts which are liquids having a melting point of 100° C. or less. Preferably, they are liquid at room temperature (18° C. to about 25° C.) or less.

OCILs in accordance with the present invention are liquid materials made from chiral compounds and/or their salt mixtures and associations thereof. "Chiral" as used herein means that the compound has at least one stereogenic center or axis (also referred to as a "chiral center" or "asymmetric center"). "Ionic" as used in connection with OCILs in accordance with the present invention includes cations, anions or salts thereof. A chiral anion is an anion which contains a stereogenic center or axis. A chiral cation is a cation which contains a stereogenic center or axis. OCILs may also be salts, mixtures or associations of both chiral cations and chiral anions. Thus a chiral anion may be associated with a nonchiral cation, thus forming a "chiral anion containing OCIL," also referred to herein as a "chiral anion" or an "anionic OCIL," or may be associated with a chiral cation. Similarly, a chiral cation may be associated with a nonchiral anion thus forming a "chiral cation containing OCIL," also referred to herein as a "chiral cation" or a "cationic OCIL" or it may be associated with a chiral anion.

Many of the compounds discussed herein are enantiomers, pairs of mirror image compounds with opposite optical configurations, (each referred to as an enantiomer or an optical isomer as appropriate). These can be present in the form of either a racemic (50:50) mixture or an optically enhanced mixtures in which one of the enantiomers is present in an amount which is greater than the other. "Optically enhanced," even when described in the context of an optically enhanced mixture, also is meant to include an optically pure material which is substantially or completely only one of the two enantiomers. The OCILs of the invention are not limited to enantiomers, but may include diastereoisomers, compounds that have more than one stereogenic center. A compound of this type with, for example, 2 stereogenic centers can be thought of for the invention as producing two distinct sets of enantiomers. Of course, while each enantiomer will be present as an equal mixture, one pair of enantiomers may be present in a greater percentage than the other. An OCIL in the case of diastereoisomers is a compound which meets the other criteria set forth herein wherein at least one of the enantiomers is present in an enhanced amount relative to its corresponding enantiomer. The other enantiomeric pair may still be racemic relative to each other, or one of optical isomers of that pair of enantiomers may also be optically enhanced. Thus it is still proper, in the context of the invention to refer to racemic mixtures and enantiomers, even though they may be diastereoisomers relative to other possible optical isomers.

One aspect of the present invention is the discovery of a novel class of chiral cationic containing OCIL molecules (often used synonymously with the term "compound" herein or as the context indicates) and in particular, those individually identified herein. Another aspect of the invention are chiral cationic containing OCILs in which at least one enantiomer is enhanced by at least about 2% relative to the other. Another aspect of the invention are chiral cationic containing OCILs in which at least one enantiomer is enhanced by at least about 10% relative to the other. Another aspect of the invention are chiral cationic containing OCILs in which at least one enantiomer is enhanced by at least about 20% relative to the other. In another aspect, the invention relates to chiral cationic containing OCIL molecules which are other than N-alkyl-N-methylephedrinium salts, and/or those shown in Table A.

Another aspect of the present invention is the discovery of a class of anionic containing OCILs. One aspect of the invention are chiral anionic OCILs in which at least one enantiomer is enhanced by at least about 2% relative to the other. Another aspect of the invention are chiral anionic containing OCILs in which at least one enantiomer is enhanced by at least about 10% relative to the other. Another aspect of the invention are chiral anionic containing OCILs in which at least one enantiomer is enhanced by at least about 20% relative to the other. In another aspect of the invention, there are provided anionic containing OCILs that are not lactates.

In yet another aspect of the present invention there is provided a class of OCILs which are salts where both anions and cations are chiral, and at least one, and preferably both, are optically enhanced. In another embodiment of this aspect of the present invention, both the cationic and anionic portions of the OCIL are chiral, but have an opposite optical rotation. Thus, for example, the cation may be (R) and the anion (S). Indeed, in this situation, there could be each of a cation with an (R) configuration, a cation with an (S) configuration, an anion with an (R) configuration and an anion with an (S) configuration, in various proportions. Thus the combinations of chiral cation and chiral anion include (R)(S), (S)(R), (R)(R), (S)(S), and preferably these are substantially pure.

In yet another aspect of the present invention there is provided a solvent that may be used for dissolving, suspending, gelling, emulsifying, dispersing and forming colloids, comprising chiral anionic, chiral cationic or mixed anionic and cationic containing OCILs. These may include those of Table A.

Another aspect of the present invention is a method of conducting a chemical reaction in the presence of at least one chiral cationic and/or chiral anionic containing OCIL. These may include those of Table A. The OCIL can be present as a part of a solvent system or as the reaction medium or carrier for one or more of the reactants or even as a reactant. Also considered part of the invention are molecules, whether chiral or achiral, racemic or not, pharmaceutically or chemically active/reactive or inert, finished product or intermediate resulting from a chemical reaction conducted in the presence of any OCIL. Preferred are non-racemic compounds synthesized asymmetrically using an OCIL in accordance with the invention. Also preferred are any reactions that are enantiomerically (or optical isomerically) selective. Also preferred are reactions using or in the presence of OCILs which involve the use of a charged species (other than the OCIL) as a reactant, reagent, intermediate or final product.

Reactions include, without limitation, condensation, hydrogenation, nucleophilic and electrophilic substitutions, deracemization, asymmetric synthesis, esterification, ether formation, halogenation, polymerization reactions, chain propagation, cross-linking, salt formation, precipitation or crystallization and the like. Deracemization and asymmetric synthesis reactions are particularly preferred. Also preferred are any reaction of the type noted immediately above that is enantiomerically (or optical isomerically) selective. Also preferred are those reactions noted immediately above using OCILs which involve the use of a charged species (other than the OCIL) as a reactant, reagent, intermediate or final product. In accordance with another aspect of the invention, any of the foregoing reactions are conducted in the presence of an OCIL which is enhanced such that it is substantially optically pure (at least 90% of one enantiomer relative to the other enantiomer). Preferably these reactions using substantially pure OCILs include asymmetric synthesis, deracimization, reactions using charged species and enantioselective processes.

A particularly preferred aspect of the present invention is an asymmetric synthesis of a compound comprising the steps of conducting a chemical reaction on at least one reactant which is in the presence of an OCIL to produce a reaction product. The reaction product is recovered and it is optically active, i.e., it has a stereogenic center or axis. One enantiomer of the reaction product will be present in an amount that is greater than the other enantiomer, usually at least about 2% difference or more (52:48%). Preferably the OCIL is the solvent. More preferably, at least a 10% difference, even more preferably at least a 20% difference, even more preferably a substantially pure OCIL is found between the content of enantiomers.

Another particularly preferred aspect of the present invention is a deracemizing reaction wherein a reactant which is in the presence of an OCIL is reacted to form a reaction product. The reactant is racemic and the reaction product, while optically active, is not racemic. Again, preferably the amount of one enantiomer is at least 2% greater than that of the other (52:48%), more preferably one reaction product is enhanced so at least about 10% more of one enantiomer is present compared to the other, even more preferably the difference is at least about 20%, and most preferred is substantially pure. Preferably the OCIL is a solvent. The asymmetric products of these reactions run in the presence of an OCIL are also claimed. These reaction products may also be separated to produce a substantially optically pure reaction product.

Another aspect of the present invention relates to the use of cationic and/or anionic OCILs as the stationary phase or support in columns prepared for chromatography including liquid chromatography, gas chromatography ("GC") and in particular capillary GC. In particular there is provided a column for use in chromatography comprising: a column and a stationary phase which is an OCIL associated therewith. Any OCIL may be used as a stationary phase. In one embodiment, the column is a capillary and the OCIL stationary phase is coated on an inner surface of said capillary. The column in accordance with the invention may also be a packed column wherein the stationary phase is absorbed, adsorbed or coated on a solid support which is packed into the column.

The invention also includes methods of separating compounds comprising the steps of: mixing, dissolving, dispersing or suspending optical isomers in a mobile phase which can be a gas or a liquid depending upon the type of chromatography, introducing the compounds to be separated into a column that includes at least one OCIL, either coated on the inside thereof or as part of a packing as a stationary phase, and advancing the mobile phase and at least one of the compounds to be separated through the column so as to resolve at least one of compounds to be separated. In a particularly preferred aspect of the invention, the compounds to be separated are optical isomers.

DETAILED DESCRIPTION

By "optically enhanced" it is understood that the chiral compounds of the invention are not present in a racemic mixture (both enantiomers present in approximately the same percentage). Instead, in accordance with the present invention, at least one of the enantiomers is present in a greater percentage. As noted previously, this applies to diastereomers as well wherein at least one of the enantiomers of one of the pairs of optical isomers which are identical but for their configuration is present in an amount that is greater than the other. More preferably, the one enantiomer is present in an amount of at least about 2.0% greater than the other enantiomer by mole percent or weight percent, as is appropriate. More preferably, one of the optical isomers will be present in an amount of at least about 10% greater than the other and even more preferably an amount of at least about 20% than the other optical isomer of a pair of enantiomers. Even more preferably, such compounds are "substantially optically pure," wherein about 90% or more of the compound in question will be a single enantiomer. This is of course relative to the other enantiomer. Diastereomers with two stereogenic centers, for example, could be substantially optically pure in the context of the invention if it had 90% of one optical isomer, 10% of its enantiomer, yet 53 percent of the total composition was a racemic mixture of the other set of enantiomers. Most preferably, an OCIL will have at least one enantiomer be present in 95% or greater relative to the other.

In the case of a mixed solvent or stationary phase of two or more chiral ionic liquids, it is not necessary that all of the liquids be optically enhanced OCILs. One or more may be racemic as long as at least one is optically enhanced.

OCILs have been found to have many uses. It has been found that they are useful as solvents, dispersants, gelling agents, emulsifying agents, colloid forming agents, and suspending agents. Indeed, because of their ability to interact on almost any level with almost any other molecule, OCILs may often be substituted, in whole or in part, for traditional organic solvents and water. OCILs can interact not only ionically, but also through, for example, dipole interaction, hydrogen bonding, pi-pi (n-n) interaction, dispersion interactions and even steric forces. This makes them useful in chemical reactions, whether used as a reactant, a solvent, or merely present during a reaction. In addition, the ability to use a material that is at least predominantly one optical isomer or another provides another dimension to research and manufacturing. It allows for potentially different interactions, using a solvent of the same chemical. The enhanced level of one optical isomer, or preferably, their substantially optically pure nature, will allow them to interact in previously unimagined ways. This is particularly true for mixtures of chiral cations and chiral anions which my have the same optical rotation of may have opposite rotations.

These OCILs are considered "green" in that they are recyclable alternatives to volatile organic solvents. They are air and moisture stable, have excellent solubilizing properties and virtually no vapor pressure. They are nonaqueous, although they can be mixed with water, and therefore can be used in a variety of situations where water is inappropriate.

OCILs in accordance with one aspect of the present invention include optically enhanced chiral cations such as, without limitation, (−)—N-Benzyl-N-methylephedrinium⁻NT₂ Isoleucine-based ILs, as either an ester or an alcohol, (−)Cotinine'TfO, D(+)-Carnitinenitrile'NTf₂, 1-((R)-1,2-propanediol)-3-methylimidazolium chloride, (−)-Scopolamine N-butyl'NTf₂ and (+)-chloromethyl methyl ether imidazolium IL. Their structures are as follows:

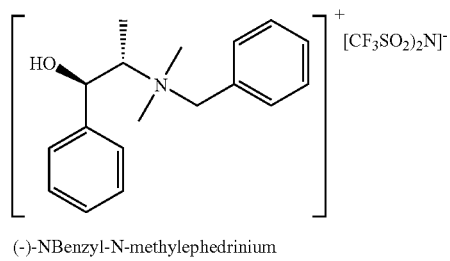

(-)-NBenzyl-N-methylephedrinium

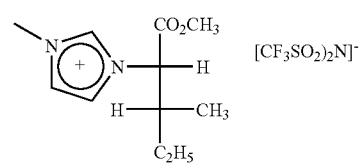

Isoleucine-based IL

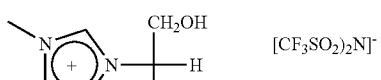

Isoleucine-based IL

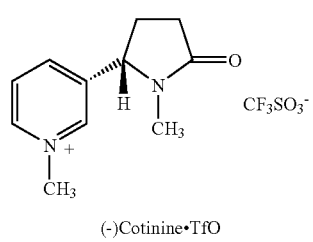

(-)Cotinine•TfO

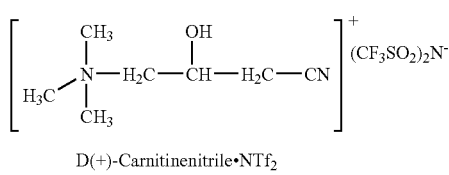

D(+)-Carnitinenitrile•NTf₂

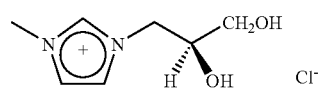

1-((R)-1,2-propanediol)-3-methylimidazolium chloride

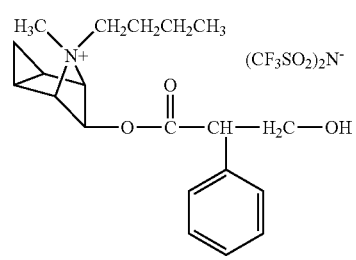

(-)-Scopolamine N-butyl NTf₂

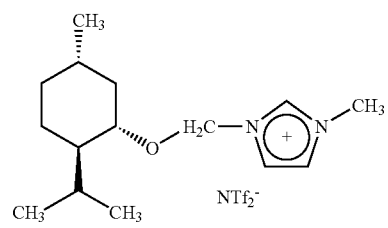

menthol substituted methyl imidazolium IL

Some of these chiral cationic containing OCILs can be produced by the following general reactions:

1. (1R,2S)-(−)-N,N-dimethylephedrinium NTf2 or (1S,2R)-(+)-N,N-dimethylephedrinium NTf2

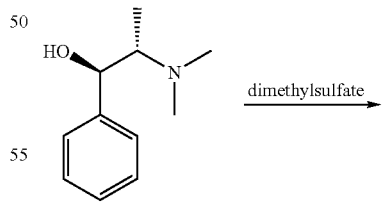

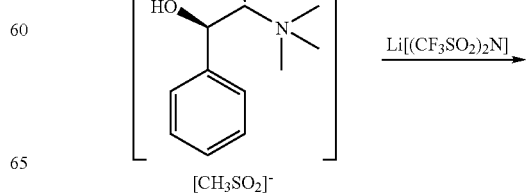

-continued
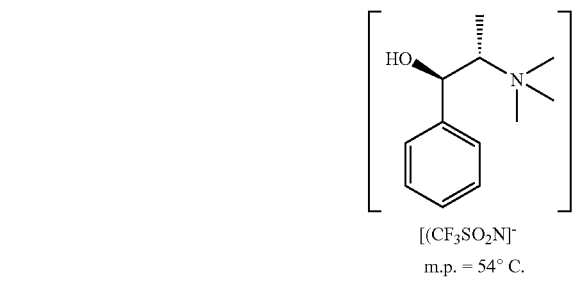
[(CF₃SO₂N)]⁻
m.p. = 54° C.
2. (−)-N-Benzyl-N-methylephedrinium NTf2
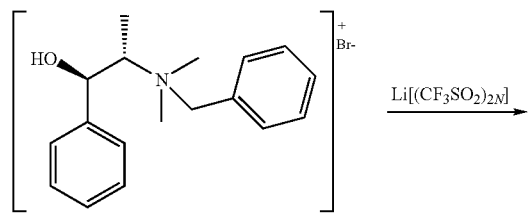
Liquid at R.T.
3. Isoleucine IL
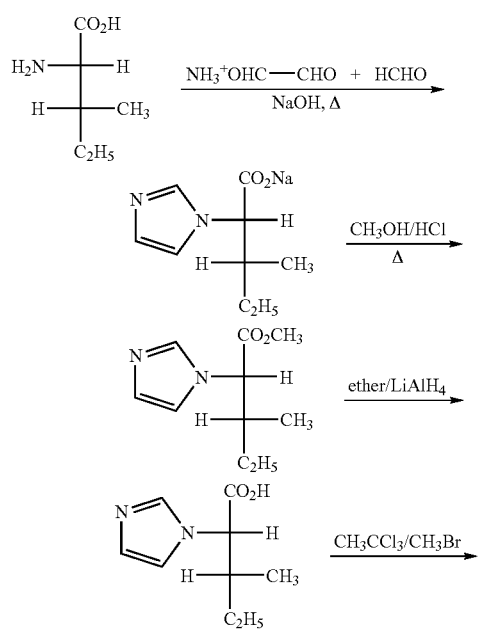
-continued
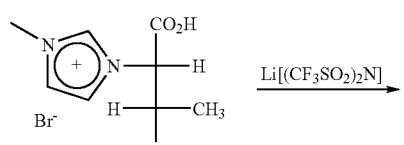
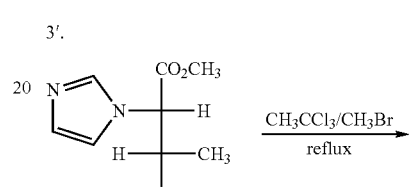
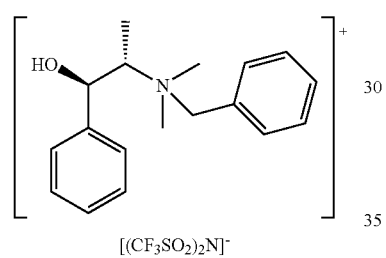
[(CF₃SO₂)₂N]⁻
Liquid at R.T.
4. N-Methyl(−)cotinine TfO
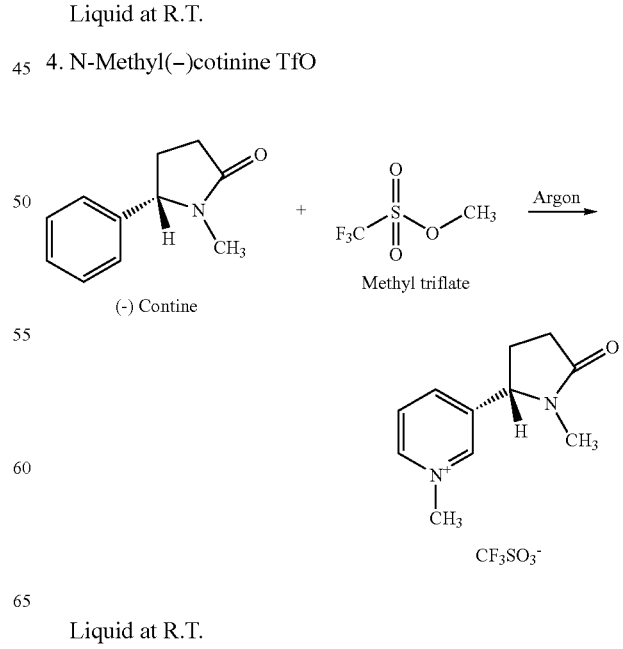
Liquid at R.T.

5. D(+)-Carnitinenitrile NTf$_2$
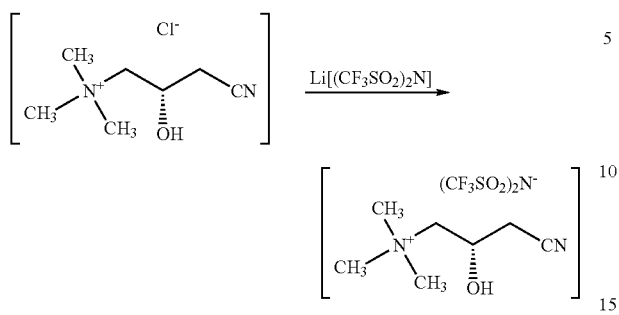
Liquid at R.T.
6. BMIM-(L-lactate)
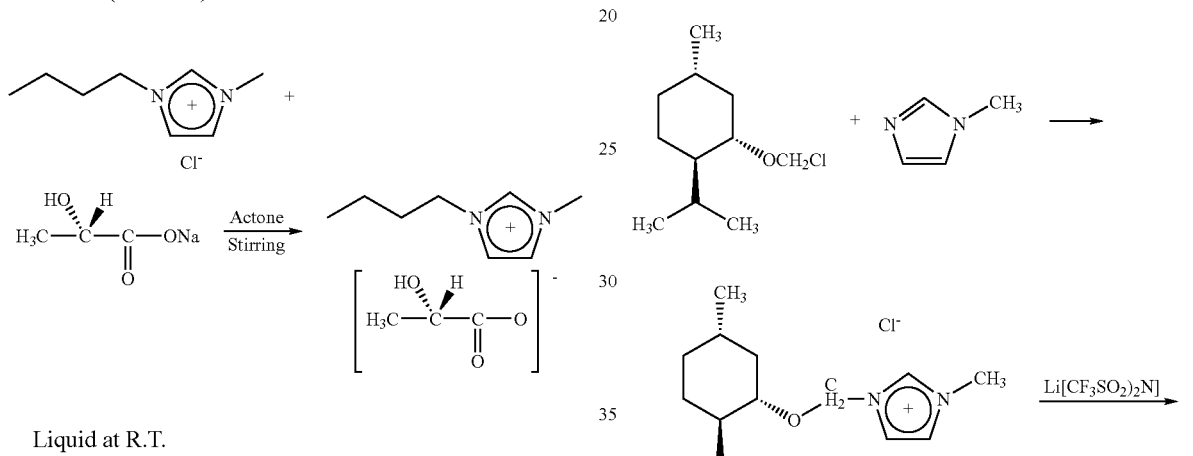
Liquid at R.T.
7. 1-((R-1,2-propanediol)-3-methylimidazolium chloride
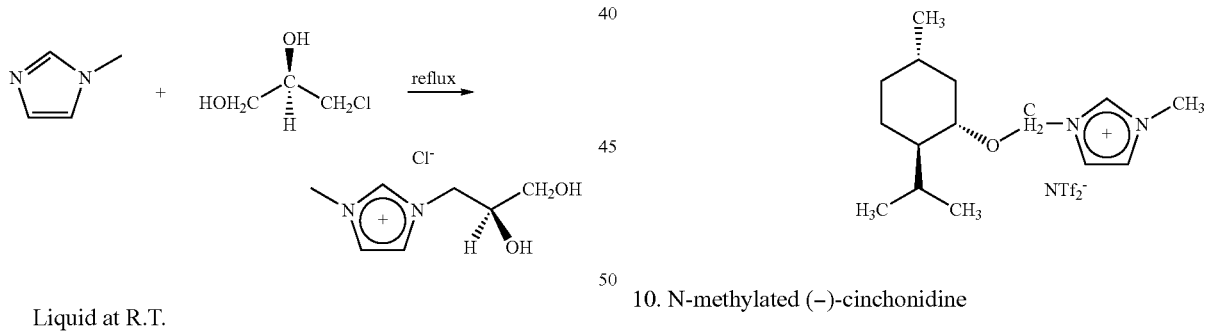
Liquid at R.T.
8. (−)-Scopolamine N-butyl NTf2
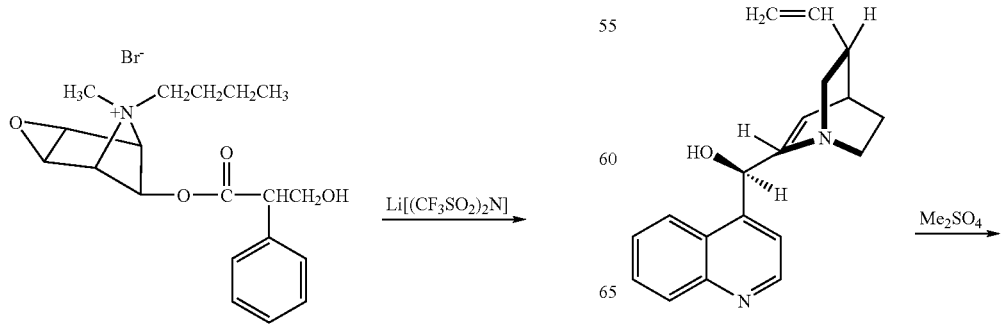
-continued
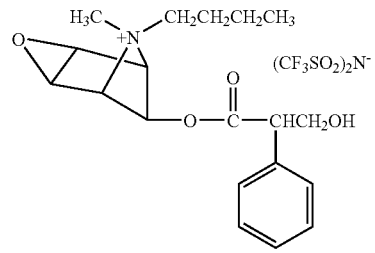
Liquid at R.T.
9. Menthol substituted methyl imidazolium
10. N-methylated (−)-cinchonidine

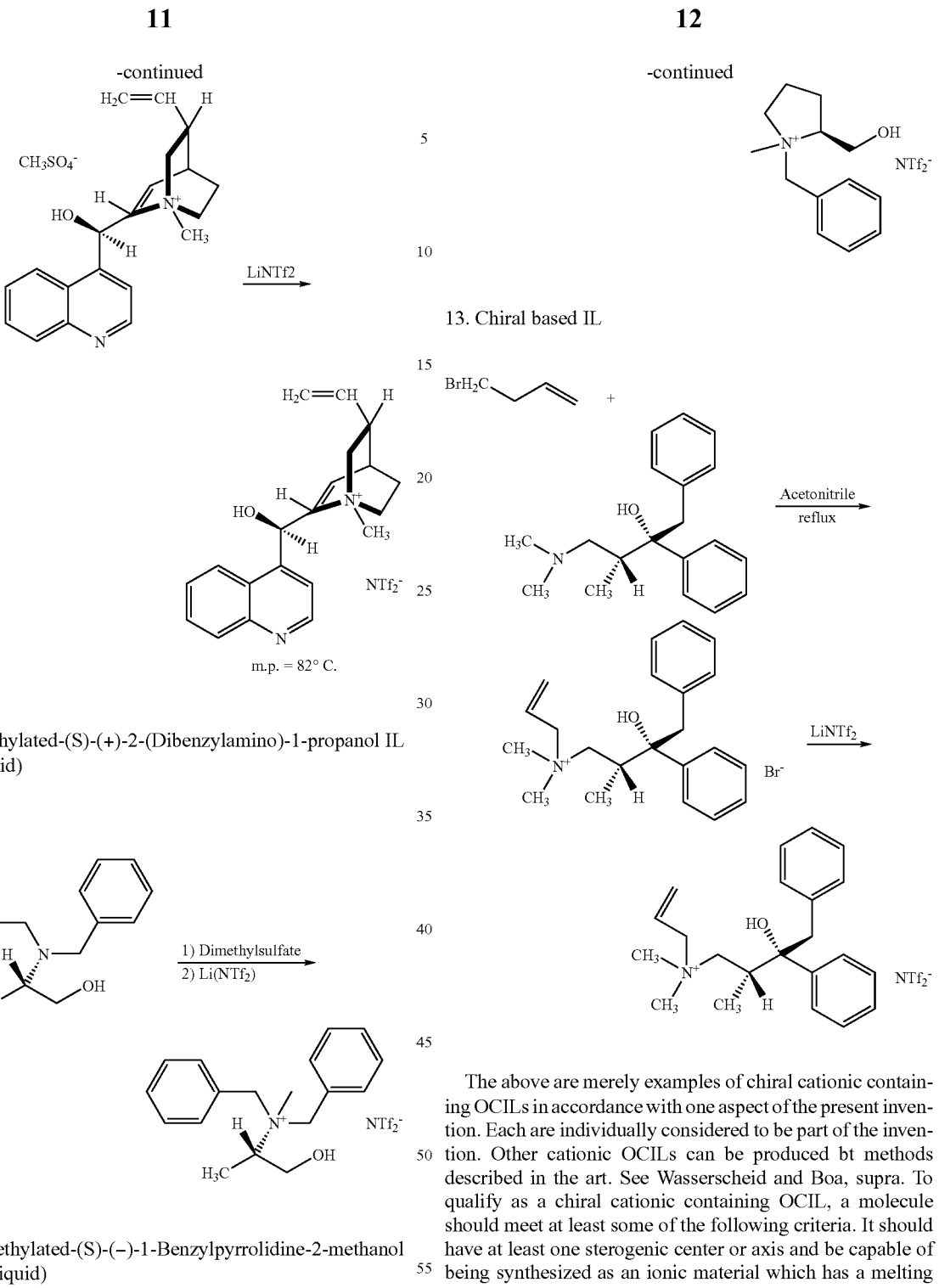

11. N-methylated-(S)-(+)-2-(Dibenzylamino)-1-propanol IL (ionic liquid)

12. N-methylated-(S)-(−)-1-Benzylpyrrolidine-2-methanol IL (ionic liquid)

13. Chiral based IL

The above are merely examples of chiral cationic containing OCILs in accordance with one aspect of the present invention. Each are individually considered to be part of the invention. Other cationic OCILs can be produced bt methods described in the art. See Wasserscheid and Boa, supra. To qualify as a chiral cationic containing OCIL, a molecule should meet at least some of the following criteria. It should have at least one sterogenic center or axis and be capable of being synthesized as an ionic material which has a melting point of 100° C. or less, and most preferably be a liquid at room temperature (18° C.-25° C.) or below. It should contain a greater amount of one optical isomer relative to tits enantiomer optical isomers of the same molecule in the system or mixture. Preferably, it is substantially optically pure. Preferably, at least 95% w/w of at least one enantiomer of the molecule is in the form of one optical isomer. To be a chiral cationic containing OCIL, it must also have a positive charge overall.

The class of novel chiral cation containing OCILs excludes these molecules as shown in Table A.

TABLE A
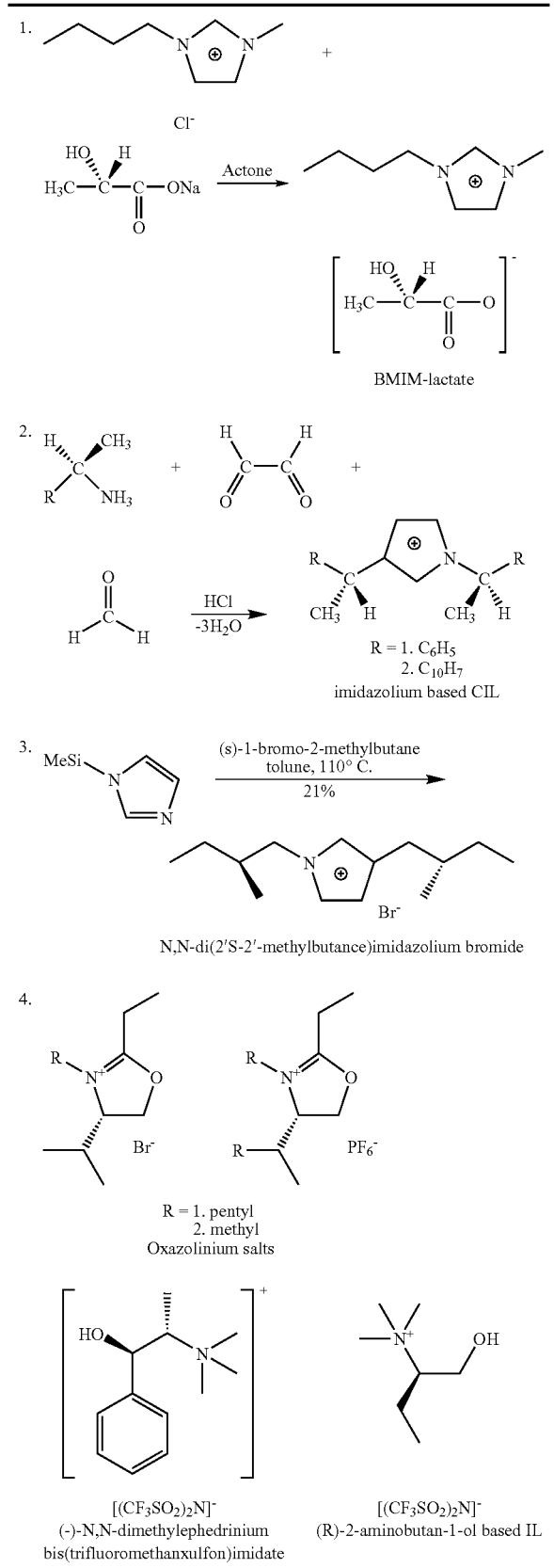
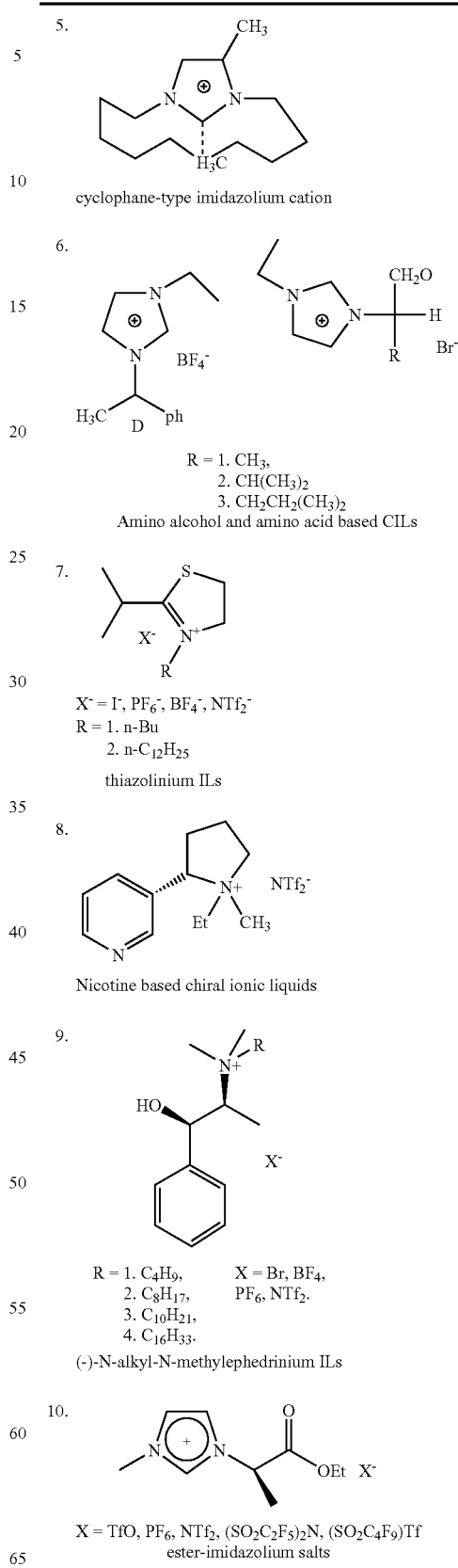

TABLE A-continued

11. 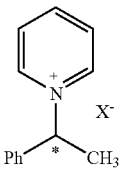

X = BF$_4$, PF$_6$, (CF$_3$SO$_2$)$_2$N
pyridimium chiral ionic liquids

12. 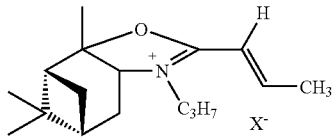

X = Br, PF$_6$, BF$_4$
CILS derived from α-Pinene

The molecules shown in Table A having an enhanced optical purity and in particular a purity whereby one enantiomer is present in an amount of at least about 10% greater than the other, more preferably 20% greater than the other, and even more preferably substantially optically pure are contemplated as part of the invention. Moreover, the use of the molecules shown in Table A as a stationary phase in chromatography, as a solvent or other use in chemical reactions described herein are also considered part of the invention.

OCILs in accordance with the present invention also include those that are anionic. These have the same overall properties as the chiral cationic containing OCILs except that they have the opposite charge. These chiral anionic containing OCILs include, but are not limited to, those with the following structures: This material can be made by the following general reaction:

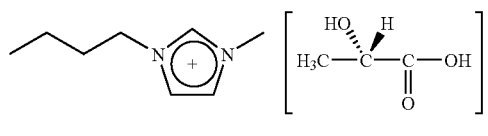

BMIM-(L-lactate)

This material can be made by the following general reaction:

6. BMIM-(L-lactate)

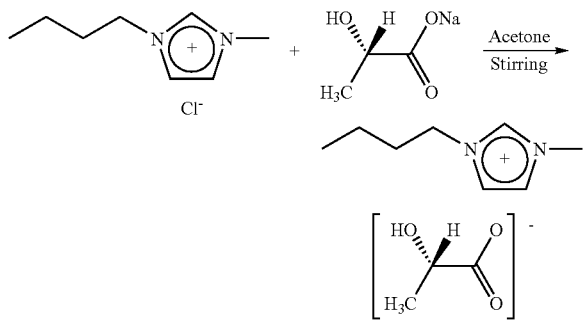

Liquid at R.T.

Other non-limiting examples of chiral anions for OCILs (illustrated with a sodium cation and thus more correctly are —O⁻ Na⁺):

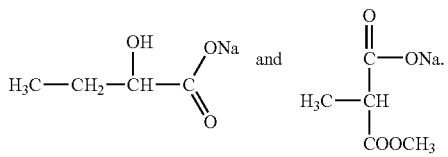

A general reaction which can be used to produce anionic OCILs is as follows:

An anion exchange reaction can take place on the OH⁻ form strong anion exchange resin between an achiral or chiral IL containing an exchangeable anion (such as Br⁻, I⁻) and the resin. And then the hydroxide IL can further react with chiral compounds by means of carboxylic acid group. This finally results in anionic OCILs.

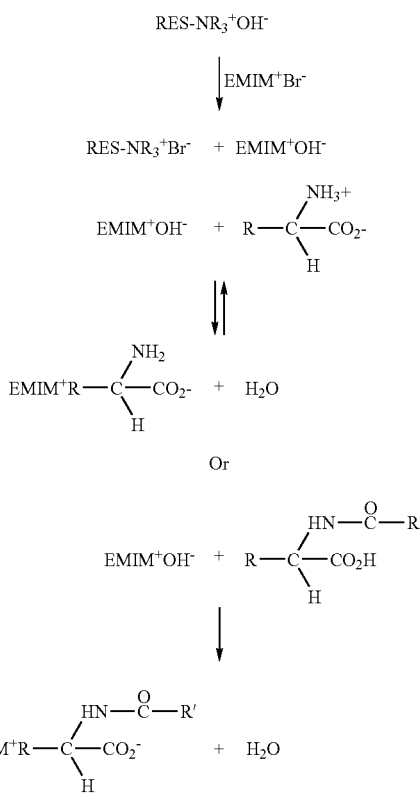

Note: 1) RES-NR$_3$+ is an anion exchange resin in the hydroxide ion form (it is a commercial product available from many places). 2) EMIM+ is ethylmethylimidazolium ion.

Salts created from either chiral cation containing OCILs and/or chiral anion containing OCILs are also included. These include an OCIL and a counter ion. Counter ions include, without limitation, PF$_6$—, [(CF$_3$SO$_2$)$_2$N—], (CF$_3$)SO$_2$⁻, Cl—, BMIM (butyl methyl imidazolium). Mixtures of these can also be created where the chiral anion containing OCIL and chiral cation containing OCIL are associated, as salts acting as counter ions for each other or disassociated. Such salts can be created from, for example, any of the anionic OCILs and cationic OCILs identified herein.

Another preferred aspect of the present invention involves conducting a chemical reaction in the presence of an OCIL, more preferably using an OCIL as a reaction medium, reaction solvent or cosolvent to form a reaction product. It is preferred that such OCILs be substantially optically pure. These reactions involve contacting or mixing one or more OCILs in accordance with the present invention with at least one reactant and causing a reaction to take place wherein some change occurs to the reactant (the "reaction product"). This change may be a change in physical state such as precipitating or melting, or may be a change in a reactant's structure such as ionization, creation of a free radical and the like. The reaction may also include chemical reorganizations and/or oxidation/reduction reactions such as transfer of an aldehyde to ketone or alcohol to acid. Movement of an unsaturated bond, a change is a resonance, etc are also contemplated. Chemical reaction can also include: hydration, condensation, hydrogenation, nucleophilic and electrophilic substitutions, cyclization, esterification, ether formation, halogenation, polymerization reactions, chain propagation, cross-linking, salt formation, crystallization, nucleophilic or electrophilic addition or substitution, saturation or unsaturation. These are just some of the reactions which are possible. While the OCILs may participate in or facilitate these reactions, they generally will not actually be a participant in that they will generally not be part of the resulting chemical. Of course, it is not unusual for solvents to be contained within various materials such as crystalline materials in the form of solvates and that is not excluded.

Reactions that can be run using OCILs in accordance with the present invention include, without limitation, the following:

Oxidation
1. Oxidation of sulfides, selenides and amines to the corresponding oxides by $NaIO_4$. plus rearrangement of the corresponding allylic oxides to allylic alcohols.
2. Oxidation of alkenes to cis-1,2-diols by $KMnO_4$, $OsO_4$, and cat. $OsO_4$ plus reoxidant.
3. Oxidation of alkenes to trans-1,2-diols by $KHSO_5.KHSO_4.K_2SO_4$ plus water.
4. Oxidation of 2-naphthols to binaphthols by $CuCl_2.4H_2O$ and $FeCl_3.6H_2O$ and oxidation of 2-naphthylamines to binaphthyl diamines by $CuCl_2.4H_2O$.
5. Olefin epoxidation by peracids; $H_2O_2$ plus urea, nitriles, tungstate, molybdate and vanadyl reagents; NaOCl plus Cr— or Mn(salen) complexes; $NaIO_4$ plus Mn(III) or cat. $RuCl_3$; $KMnO_4$ plus $CuSO_4$; methyltrioxorhenium and $KHSO_5.KHSO_4.K_2SO_4$.
6. Kinetic resolution of 2° alcohols (1-phenylethyl alcohol and 2-butanol) by oxidation with $KMnO_4$, tetra-N-propylammonium perruthenate and other oxidants.

Reductions
1. Reduction of ketones [PhCOMe and ethyl acetoacetate as model systems] to alcohols by $NaBH_4$, $NaHB(OMe)_3$, $NaHB(OAc)_3$ and $NaH_3BCN$.
2. Reductive amination of ketones [PhCOMe and cyclohexyl methyl ketone as model systems] by various 1° and 2° amines using $NaH_3BCN$.

Pericyclic Reactions
1, Diels-Alder, hetero Diels-Alder and inverse electron-demand Diels-Alder reactions, particularly reactions that are reversible like those of furan not run in lactate.
2. Cope and oxy-Cope rearrangements.
3. Claisen rearrangement.

PD-Catalyzed Processes
1. Alkylation of allylic acetates by amines, stabilized carbanions and other nucleophiles.
2. Inter- and intramolecular Heck reactions using aryl halides/triflates, cycloalkenes and Pd(0).
3. Reaction of ArI(OTf) with $R^1CH=CR^2CHR^3OH$ to give $ArCHR^1CHR^2COR^3$.
3. Suzuki reaction of hindered aryl halides/triflates and arylboronic acids to form atropisomers.
4. Pd(II)-catalyzed cyclization of 2-allylic phenols to 2,3-dihydrobenzofurans.
5. Pd(0)-catalyzed annulation of 1,2-, 1,3-, and 1,4-dienes by 2-haloanilines and -phenols.
6. Hydroesterification of styrenes to 2-arylpropionic acids and esters.

Other Transition Metal-Catalyzed Processes
1. Hydroformulation of internal olefins [cis-3-hexene, cyclopentene and cyclohexene].
2. Hydrogenation of $RR'C=CH_2$, $H_2C=C(NHAc)CO_2H$ (R), $H_2C=CArCO_2H(R)$ and Baylis-Hillman adducts.
3. Pauson-Khand reaction.
4. Conversion of $RCH=CH_2$ and $N_2CHCO_2R'$ to cyclopropane esters.
5. Inter- and intramolecular hydroamination and hydroalkoxylation of alkenes by $PtCl_2$ or $Zn(OTF)_2$.

Condensation Reactions
1. Michael reactions [cyclohexenone and $MeCOCH_2COMe$ or $EtO_2CCH_2CO_2Et$].
2. Aldol [MeCHO] reaction.
3. Claisen condensation [ethyl propionate and ethyl phenylacetate].
4. Henry reaction of aldehydes [MeCHO and PhCHO] with nitroalkanes [$MeNO_2$].
5. Baylis-Hillman reaction [PhCHO and acrylates, acrylonitrile and methyl vinyl ketone using DABCO and $Bu_3P$].
6. Cyanohydrin and silyl cyanohydrin formation from aldehydes [PhCHO].
7. Strecker synthesis of $RCH(NH_2)CN$ from RCHO, $NH_3$ and HCN.
8. Passerini synthesis of $R^1CH(O_2CR^2)CONHR^3$ from $R^1CHO$, $R^2CO_2H$ and $R^3NC$.
9. Ugi synthesis of $R^1CH(NHR^4COR^2)CONHR^3$ from $R^1CHO$, $R^2CO_2H$ and $R^3NC$ and $R^4NH_2$.
10. $Sc(OTf)_3$-catalyzed condensation of ArCHO, $PhNH_2$ and $P(OEt)_3$ to industrially important $ArCH(NHPh)PO(OEt)_2$.

Alkylation Reactions
1. Alkylation of enamines [cyclohexanone pyrrolidine enamine and MeI].
2. Alkylation of unsymmetrical dicarbonyl compounds [ethyl acetoacetate, $PhCOCH_2CO_2Et$, $PhCOCH_2COCH_3$].
3. Friedel-Crafts arylation by 2° alkyl halides and triflates in non-alcohol containing CILs.

Other Organic Reactions
1. $S_N2$ reactions of 2° alkyl halides [PhCHBrMe model system] with various nucleophiles [NaOAc, $NaN_3$, NaOMe, NaSPh, NaOPh and Na(acac)] for the kinetic resolution of organic halides and synthesis of chiral products.
2. $S_N2$ ring opening of symmetrical epoxides [cis-2-butene oxide, cyclopentene oxide] by various nucleophiles.
3. Kinetic resolution of 2° alkyl esters [2° butyl and phenethyl acetates and benzoates] by hydrolysis and transesterification [MeOH and EtOH].

Particularly preferred are those reactions discussed above that are enantiomerically selective (applicable to diastereomers as noted previously) those that involve a changed reactant, reagent, intermediate or product, other than the OCIL.

Also preferred are those reactions run in an OCIL that is substantially optically pure (at least 90 of one enantiomer relative to the other) as well as those run using chiral cationic containing OCILs and chiral anionic containing OCILs that are not lactates. Combinations of these are also preferred, such as, by way of a non-limiting example, those enantiomerically selective reactions run in a chiral anionic containing OCIL that is substantially optically pure. Many of these reactions, run in an OCIL, are particularly preferred as they permit the asymmetric synthesis of one enantiomer over another. This is a particularly preferred aspect of the invention.

A particularly preferred type of reaction in accordance with the present invention is deracemization. A deracemization reaction allows for the transformation of a racemic mixture of a chiral carbon-containing compound to a mixture in which one optical isomer predominates. Preferably, the one resulting optical isomer will be present in an amount greater than any other optical isomer of the same compound present. In a racemic mixture of enantiomers from a single chiral center, following a reaction in the presence of an OCIL, preferably one enantiomer will be provided in an amount greater than 50% with the balance being the other. In a particularly preferred aspect of the present invention, the deracemization reaction provides at least a 10% increase in the relative percentage of one enantiomer versus the other. More preferably, the deracemization reaction provides for a significant increase in one optical isomer over another. Even more preferred, the resulting mixture is substantially enantiomerically pure (90% or greater). Most preferably, the reaction in the presence of an OCIL will produce an enantiomerically pure material (99% of one optional isomer or more).

An example of a deracemization reaction run using an OCIL is:

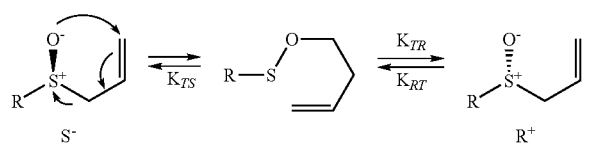

This is a thermal racimization/deracimization reaction of a chiral vinyl sulfoxide. The reactant exists as a racemate, a 50:50 mixture of enantiomers, at equilibrium. By dissolving this reactant into an OCIL in accordance with the present invention (both N,N-dimethylephedrinium and (−)-N-benzyl-N-methylephedrinium were used successfully) and heating to 50° C.-75° C., followed by cooling to room temperature, deracemization occurred.

Without wishing to be bound by any theory of appreciation, it is believed that the reason the deracemization works so well, is the fact that the sulfoxide to sulfonate rearrangement is reversible and the OCIL more strongly binds to one of the sulfoxide enantiomers than the other, which eventually allows one to convert more of the racemate into one enantiomer. Other factors which are believed to favor one enantiomer over the other include unique ability of OCILs to hydrogen bond through a neighboring alcohol group to functionality in the substrate, further stabilizing one OCIL complex over another. This may be the driving force behind the relatively high enantioselectivity of the photochemical rearrangement discussed earlier.

Another preferred reaction in accordance with the present invention is a reaction wherein a nonchiral or achiral starting material is reacted and converted into a chiral product, Even more preferably, the resulting chiral product is not a racemate. One of the optical isomers will predominate. An example of such a reaction run using an OCIL is:

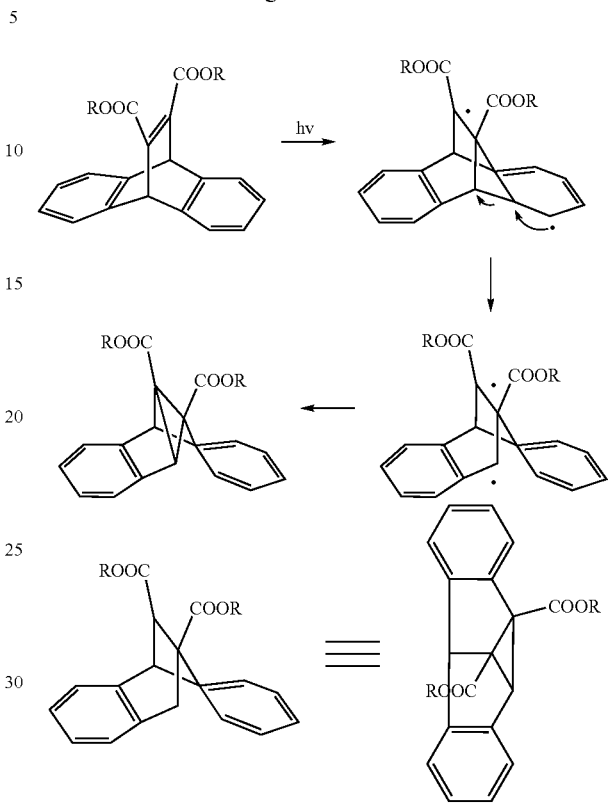

R = CH₃ or H

The starting material was achiral. After a reaction in conventional solvents, a racemic mixture would result. However, when run in an OCIL in accordance with the present invention, ((+)-chloromethyl methyl ether imidazolium IL), with UV applied at about 254 nm at room temperature, one of the optical isomers predominated (60:40). This reaction has also been run in N,N-dimethylephedrinium and resulted in an increase in the percentage of one enantiomer.

Other forms of asymmetric synthesis (producing one optical isomer in greater quantities relative to others) in the presence of an OCIL are a preferred embodiment of this aspect of the invention. A non-limiting list of such reactions was provided above.

Another preferred embodiment in accordance with the present invention involves the use of OCILs as the stationary phase in columns used in liquid chromatography (LC, HPLC) and gas chromatography ("GC"), preferably capillary columns used in gas chromatography. These can be used for separation of optical isomers of chiral materials. Because of their ionic character, OCILs may be used to separate materials which even chiral, but nonionic materials, cannot separate. Any OCIL may be used in accordance with the present invention including PCOCILs and anionic OCILs.

OCILs may be coated onto capillary columns as follows. The entire column is filled with a solution, typically of a cosolvent such as methylene chloride, diethyl ether or pentane) mixed with an OCIL having a concentration appropriate for the deposition of a film of the desired thickness. Typical concentrations of the OCIL is between 0.2-0.3%. This, however, may vary as needed. After filling, one end of the column is sealed, and the other end is connected to a high vacuum pump with an adjustment valve and placed in a water bath. As the volatile non-OCILs slowly evaporate, the solvent front in the capillary retreats back down the fused silica tube leaving a coating of OCILs on the wall. The procedure is continued (with periodic increases in the vacuum to keep the vaporization rate constant) until all the cosolvent has evaporated and, except for an even coating of the OCILs, now called a stationary phase, the column is empty. These columns are then placed into and used in various gas chromatographs in accordance with particular procedures which may be unique to the separation techniques employed and/or to the equipment used.

The synthesis of (1S,2R)-(+)-N,N-dimethylephedrinium trifluoromethanesulfonimide, (1R,2S)-(−)-N,N-dimethylephedrinium trifluoromethanesulfonimide, (1S,2S)-(+)-N,N-dimethylpseudoephedrinium trifluoromethanesulfonimide are described elsewhere.[22] Briefly, N-Methylephedrine is dissolved in dichloromethane and equimolar dimethyl sulfate is slowly added. The solvent is removed under reduced pressure and the residue dissolved in water. Addition of an aqueous solution of equimolar of lithium trifluoromethanesulfonimide will lead to the separation of an ionic liquid phase which then is washed three times with water. The final product is heated under reduced pressure at 100° C. to eliminate remaining water.

All capillary columns are coated by static coating method at 40° C. using a 0.25% (w/v) of the IL stationary phase dissolved in dichloromethane. Following the coating process, the coated columns are flushed with dry helium gas overnight and conditioned from 40 to 120° C. at 1° C./min. Column efficiency is tested by naphthalene at 100° C. All columns used will have an efficiency of over 2100 plates/meter.

The racemic test compounds are dissolved in dichloromethane. A Hewlett-Packed model 6890 gas chromatograph and a Hewlett-Packard 6890 series integrator is used for all separations. Split injection and flame ionization detection are utilized with injection and detection temperatures of 250° C. Helium is used as the carrier gas with a flow rate of 1.0 mL/min.

A large number of compounds have been injected into the OCIL columns like those discussed above, which included alcohols, amines, organic acids and oxides. The racemic mixtures listed in Table 1 can be enantiomerically resolved on the OCIL stationary phases. The chromatograms were obtained on an 8 meters (1S,2R)-(+)-N,N-dimethylephedrinium trifluoromethanesulfonimide column.

TABLE 1

Separation of compounds on (1S,2R)-(+)-N,N-diemthylephedrinium-bis(trifluoromethanesulfon)imidate column*

| # | Compound | Structure | T(° C.) | $\kappa_1$ | $\alpha$ |
|---|---|---|---|---|---|
| 1 | Sec-Phenethyl alcohol | 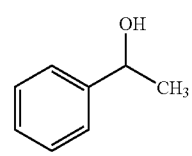 | 120 | 7.64 | 1.11 |
| 2 | 1-Phenyl-1-propanol | 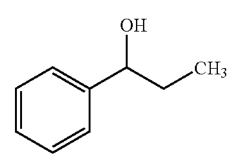 | 120 | 10.1 | 1.11 |
| 3 | 1-Phenyl-1-butanol | 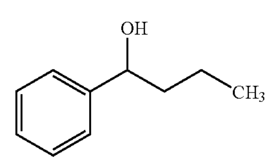 | 120 | 15.3 | 1.07 |
| 4 | α-Cyclopropylbenzyl alcohol | 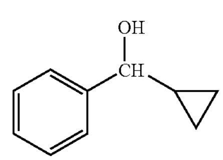 | 100 | 37.4 | 1.03 |
| 5 | α-Phenyl ethyl amine (TFA derivative) | 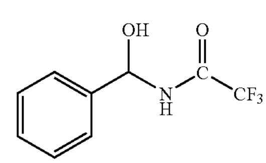 | 100 | 84.1 | 1.02 |

TABLE 1-continued

Separation of compounds on (1S,2R)-(+)-N,N-diemthylephedrinium-bis(trifluoromethanesulfon)imidate column*

| # | Compound | Structure | T(° C.) | $\kappa_1$ | $\alpha$ |
|---|---|---|---|---|---|
| 6 | β-Pinene Oxide | 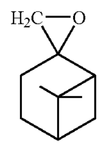 | 100 | 12.3 | 1.03 |
| 7 | o-Methylphenylmethyl | 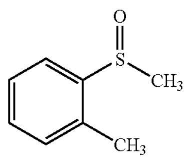 | 140 | 73.3 | 1.03 |
| 8 | o-Chlorophenylmethyl sulfoxide | 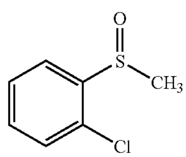 | 140 | 35.4 | 1.02 |
| 9 | o-Bromophenylmethyl sulfoxide | 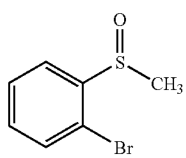 | 140 | 59.2 | 1.02 |
| 10 | m-Methylphenylmethyl sulfoxide | 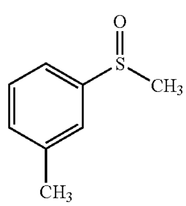 | 120 | 241 | 1.01 |
| 11 | m-Chlorophenylmethyl sulfoxide | 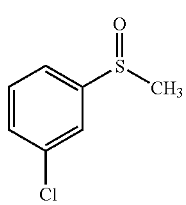 | 120 | 196 | 1.01 |
| 12 | m-Bromophenylmethyl sulfoxide | 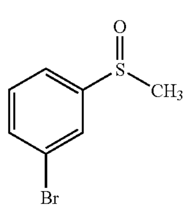 | 120 | 374 | 1.01 |
| 13 | trans-1,2-cyclohexandiol | 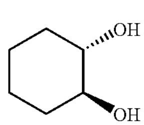 | 120 | 21.4 | 1.10 |

TABLE 1-continued

Separation of compounds on (1S,2R)-(+)-N,N-diemthylephedrinium-bis(trifluoromethanesulfon)imidate column*

| # | Compound | Structure | T(° C.) | $\kappa_1$ | $\alpha$ |
|---|---|---|---|---|---|
| 14 | trans-2-Phenyl-1-cyclohexanol | (cyclohexane with OH and Ph substituents) | 100 | 100 | 1.02 |

*Column length: 8 meters, flow rate: 1 ml/min
$\kappa_1$ is the retention factor for the first enantiomer
$\alpha$ is the ratio of retention times for the enantiomers All of the compounds listed in Table 1 can form hydrogen bonds with the hydroxyl group on the first chiral center of the chiral ionic liquid stationary phase A 13 meter (1S,2R)-(+)-N,N-dimethylephedrinium trifluoromethanesulfonimide column was chosen to undergo a TFA derivatization process.[24] The new column was then tested against all the compounds in Table 1. The experimental results showed that only the sulfoxides can be resolved enantiomerically. Nevertheless, the enantioselectivity became worse. It was also determined that the hydroxyl group on the first chiral center of the chiral stationary phase in this instance was important for the chiral recognition. While the forgoing separations were conducted using gas chromatography, OCILs may be used in the same way in liquid chromatography, including high performance liquid chromatography or HPLC.

Example 1

A reaction gives about 3% enantiomeric excess (e.e.) when the N,N-dimethylephedrinium.NTf2 were used as a cosolvent. The reaction is a reduction of methyl phenyl ketone by NaBH.sub.4 run at room temperature. The reaction mixture was analyzed by GC using a 20 m Chiraldex™ G-PN column.

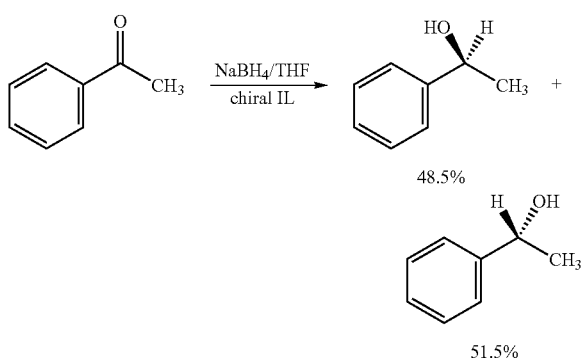

REFERENCES

1. Fishcer, T.; Sethi, A.; Welton, T.; Woolf, J. *Tetrahedron Lett.* 1999, 40, 793.
2. Lee, C. W. *Tetrahedron Lett.* 1999, 40, 2461.
3. Ludley, P.; Karodia, N. *Tetrahedron Lett.* 2001, 42, 2011.
4. Earle, M. J.; McCormac, P. B.; Seddon, K. R. *Green Chemistry.* 1999, 1, 23.
5. Adams, C. J.; Earle, M. J.; Roberts, G.; Seddon, K. R. *Chem. Commun.* 1998, 2097.
6. Stark, A.; Maclean, B. L.; Singer, R. D. *J. Chem. Soc., Dalton Trans.* 1999, 63.
7. Chauvin, Y. L.; Mussmann, L.; Olivier, H. *Angew. Chem. Int. Ed. Commun.* 1996, 34, 2698.
8. Saurez, P. A. Z.; Dullius, J. E. L.; Einloft, S.; Souza R. F. de; Dupont, J. *Polyhedron,* 1996, 15, 1217.
9. *Agueous-Phase Organometallic Catalysis: Concepts and Applications*; Cornils, B., Herrmann, W. A., Eds.; Wiley-VCH; Weinheim, 1998.
10. Huddleston, J. G.; Willauer, H. D.; Swatloski, R. P.; Visser, A. E.; Rogers, R. D. *Chem. Commun.* 1998, 1765.
11. Branco, L. C.; Crespo, J. G.; Afonso, C. A. M. *Angew. Chem. Int. Ed. Commun.* 2002, 41, 2771.
12. Armstrong, D. W.; He, L.; Liu, Y.-S. *Anal. Chem.* 1999, 71, 3873.
13. Anderson, J. L.; Armstrong, D. W. *Anal. Chem.* 2003, 75, 48-51.
14. Barber, D. W.; Phillips, C. S. G.; Tusa, G. F.; Verdin, A. *J. Chem. Sco.* 1959, 18.
15. Pachole, F.; Butler, H. T.; Poole, C. F. *Anal. Chem.* 1982, 54, 1938.
16. Poole, C. F.; Butler, H. T.; Coddens, M. E.; Dhanesar, S. C.; Pacholec, F. *J. Chromatogr.* 1984, 289, 299.
17. Furton, K. G.; Poole, C. F. *Anal. Chem.* 1987, 59, 1170.
18. Pomaville, R. M.; Poole, C. F. *Anal. Chem.* 1988, 60, 1103.
19. Poole, S. K.; Poole, C. F. *Analyst* 1995, 120, 289-294.
20. Berthod, A.; He, L.; Armstrong, D. W. *Chromatographia* 2001, 53, 63.
21. Howarth, J.; Hanlon, K.; Fayne, D.; McCormac, P. *Tetrahedron Lett.* 1997, 38, 3097.
22. Wasserscheid, P.; Bösmann, A.; Bolm, C. *Chem. Commun.* 2002, 200.
23. Bao, W.; Wang, Z.; Li, Y. *J. Org. Chem.* 2003, 68, 591.
24. Chiraldex handbook, 6th edition, *Advanced Separation Technologies,* 2002, 8.

The invention claimed is:

1. A method for identifying an optically enhanced chiral ionic liquid (OCIL) for enantiomeric resolution, the method comprising:
   a. forming a stationary phase on a column comprising a test OCIL;
   b. injecting a mixture of two or more chiral optical isomers into the column;
   c. advancing a mobile phase comprising said optical isomers through the column;
   d. detecting retention times of said optical isomers;
   e. calculating ratio of retention times between two or more of said optical isomers ($\alpha$-value); and
   f. selecting an OCIL having an $\alpha$-value greater than 1.00.

2. The method of claim 1, wherein the α-value is in a range from about 1.01 to about 1.11, inclusive.

3. The method of claim 1, wherein the mobile phase further comprises a carrier gas.

4. The method of claim 3, wherein the carrier gas is helium with a flow rate of about 1.0 mL/min.

5. The method of claim 1, wherein the mobile phase is present at a temperature in the range of about 100° C. to about 140° C., inclusive.

6. The method of claim 1, wherein the injecting comprises split injection.

7. The method of claim 6, wherein the detecting comprises flame ionization detection.

8. The method of claim 7, wherein the split injection and the flame ionization detection are utilized with injection and detection temperatures of about 250° C.

9. The method of claim 1, wherein the mobile phase further comprises helium with a flow rate of about 1.0 mL/min at a temperature in the range of about 100° C. to about 140° C., inclusive.

10. The method of claim 9, wherein the injecting comprises split injection at a temperature of about 250° C., and the detecting comprises flame ionization detection at a temperature of about 250° C.

* * * * *

UNITED STATES PATENT AND TRADEMARK OFFICE
CERTIFICATE OF CORRECTION

| | | |
|---|---|---|
| PATENT NO. | : 7,776,582 B2 | Page 1 of 4 |
| APPLICATION NO. | : 12/331108 | |
| DATED | : August 17, 2010 | |
| INVENTOR(S) | : Daniel W. Armstrong et al. | |

It is certified that error appears in the above-identified patent and that said Letters Patent is hereby corrected as shown below:

(1) Column 7, line 22, incorrectly reads "Li[(CF$_3$SO$_2$)$_{2N}$]" whereas it should read --Li[(CF$_3$SO$_2$)$_2$N]--;

(2) Column 7, line 61, incorrectly reads "CO$_2$H" whereas it should read --CH$_2$OH--;

(3) Column 8, line 4, incorrectly reads "CO$_2$H" whereas it should read --CH$_2$OH--;

(4) Column 8, line 12, incorrectly reads "CO$_2$H" whereas it should read --CH$_2$OH--;

(5) Column 8, line 50, incorrectly reads " 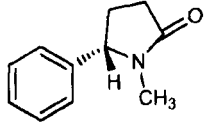 " whereas it should read -- 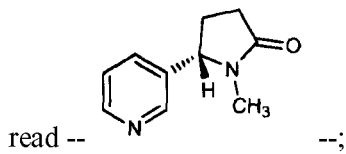 --;

(6) Column 9, line 27, incorrectly reads "Actone" whereas it should read --Acetone--;

(7) Column 10, line 55, incorrectly reads " 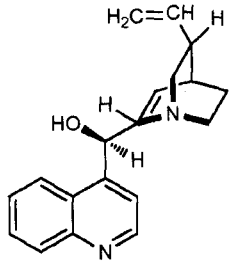 " whereas it

Signed and Sealed this
Eighteenth Day of January, 2011

David J. Kappos
*Director of the United States Patent and Trademark Office*

CERTIFICATE OF CORRECTION (continued)
U.S. Pat. No. 7,776,582 B2 should read -- 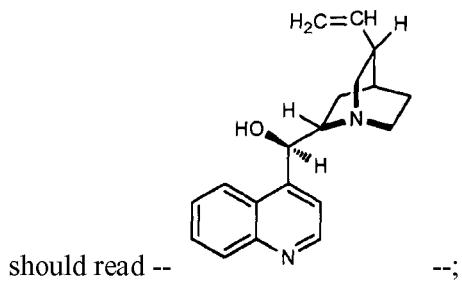 --;

(8) Column 11, line 5, incorrectly reads " 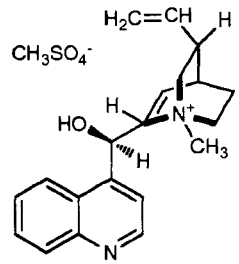 " whereas it should read -- 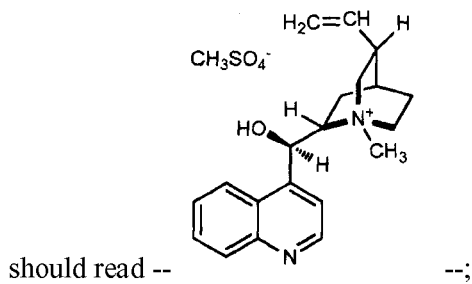 --;

(9) Column 11, line 16, incorrectly reads " 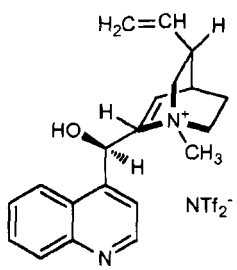 " whereas it should read -- 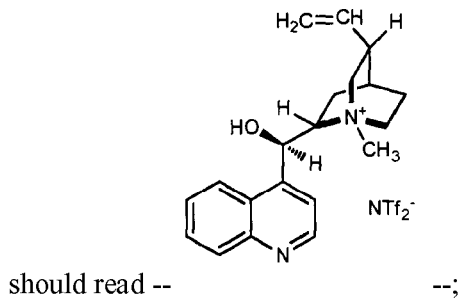 --;

CERTIFICATE OF CORRECTION (continued)
U.S. Pat. No. 7,776,582 B2

(10) Column 12, line 30, incorrectly reads " 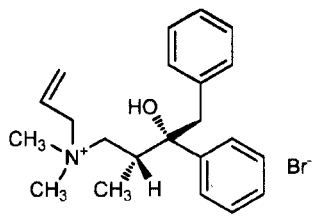 " whereas it should read -- 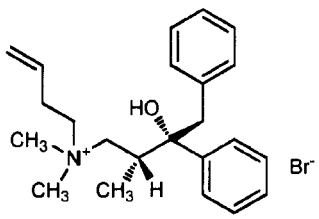 --;

(11) Column 12, line 40, incorrectly reads " 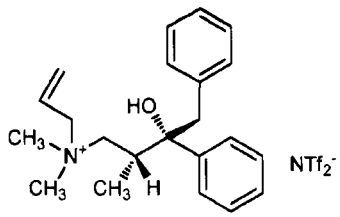 " whereas it should read -- 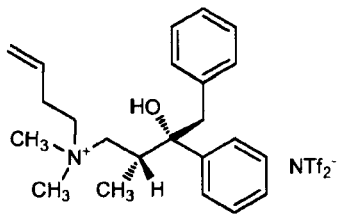 --;

(12) Column 12, line 50, incorrectly reads "produced bt" whereas it should read --produced by--;

(13) Column 12, line 54, incorrectly reads "one sterogenic" whereas it should read --one stereogenic--;

(14) Column 12, line 58, incorrectly reads "relative to tits" whereas it should read --relative to its--;

(15) Column 13, line 10, incorrectly reads "Actone" whereas it should read --Acetone--;

(16) Column 13, line 25, incorrectly reads " 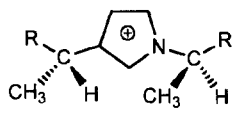 " whereas it should read -- 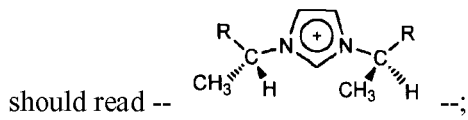 --;

CERTIFICATE OF CORRECTION (continued)
U.S. Pat. No. 7,776,582 B2

(17)  Column 13, line 35, incorrectly reads "tolune" whereas it should read --toluene--;

(18)  Column 14, line 3, incorrectly reads "$CH_2O$" whereas it should read --$CH_2OH$--;

(19)  Column 14, line 19, incorrectly reads "ph" whereas it should read --Ph--;

(20)  Column 22, Table 1 header reads "diemthylephedrinium" whereas it should read --dimethylephedrinium--;

(21)  Column 23, Table 1 header reads "diemthylephedrinium" whereas it should read --dimethylephedrinium--; and

(22)  Column 25, Table 1 header reads "diemthylephedrinium" whereas it should read --dimethylephedrinium--.